United States Patent [19]

Bourke et al.

[11] Patent Number: 5,637,320

[45] Date of Patent: Jun. 10, 1997

[54] CONTROLLED ABSORPTION NAPROXEN FORMULATION FOR ONCE-DAILY ADMINISTRATION

[75] Inventors: Edward A. Bourke; Seamus Mulligan, both of Athlone, Ireland

[73] Assignee: Elan Corporation, PLC, Athlone, Ireland

[21] Appl. No.: 227,566

[22] Filed: Apr. 14, 1994

Related U.S. Application Data

[63] Continuation of Ser. No. 70,659, Jun. 1, 1993, abandoned, which is a continuation of Ser. No. 641,441, Jan. 14, 1991, abandoned.

[30] Foreign Application Priority Data

Jan. 15, 1990 [IE] Ireland ..................... 149/90

[51] Int. Cl.$^6$ ..................... A61K 9/54
[52] U.S. Cl. ............ 424/489; 424/451; 424/459; 424/458; 424/457; 424/464; 424/469; 424/468; 424/471; 424/490
[58] Field of Search ............ 424/489, 474, 424/472, 475, 468, 490, 451, 459, 458, 457, 464, 469, 471

[56] References Cited

U.S. PATENT DOCUMENTS

| | | | |
|---|---|---|---|
| 4,783,337 | 11/1988 | Wong et al. | 424/468 |
| 4,803,079 | 2/1989 | Hsiao et al. | 424/468 |
| 4,867,984 | 9/1989 | Patel | 424/489 |
| 5,024,842 | 6/1991 | Edgren | 424/489 |

FOREIGN PATENT DOCUMENTS

| | | | |
|---|---|---|---|
| 0147780 | 7/1985 | European Pat. Off. | A61K 9/32 |
| 255002 | 2/1988 | European Pat. Off. | |
| 0255002 | 2/1988 | European Pat. Off. | A61K 9/22 |
| 0274734 | 7/1988 | European Pat. Off. | A61K 9/24 |
| 313328 | 4/1989 | European Pat. Off. | |
| 0313328 | 4/1989 | European Pat. Off. | A61K 9/46 |
| 0324981 | 7/1989 | European Pat. Off. | A61K 9/22 |
| 2180154 | 3/1987 | United Kingdom | A61K 9/14 |
| 2203338 | 10/1988 | United Kingdom | |

OTHER PUBLICATIONS

J.G. Kelly, C.D. Kinney, J.G. Devane, S. Mulligan & B.V. Colgan—"Pharmacokinetic properties and clinical efficacy of once–daily sustained–release naproxen", Eur. J. Clin. Pharmacol (1989) 36:383–388.

*Primary Examiner*—Raj Bawa
*Attorney, Agent, or Firm*—Marla J. Church

[57] ABSTRACT

A once-daily naproxen formulation for oral administration having a first portion of the naproxen as a multi-particulate pellet form, each pellet having a core of naproxen or a pharmaceutically acceptable salt thereof in association with an organic acid, the core being surrounded by a multi-layer membrane and optionally a second portion of naproxen formulated to release the drug promptly following oral administration.

17 Claims, 1 Drawing Sheet

CONTROLLED ABSORPTION NAPROXEN FORMULATION FOR ONCE-DAILY ADMINISTRATION

This application is a continuation of application Ser. No. 08/070,659, filed Jun. 1, 1993, now abandoned, which is a continuation of application Ser. No. 07/641,441 filed Jan. 14, 1991, now abandoned.

BACKGROUND OF THE INVENTION

This invention relates to a controlled absorption pharmaceutical formulation and, in particular, to a controlled absorption form of naproxen for oral administration.

FIELD OF INVENTION

Naproxen, a propionic acid derivative ((S)-6-methoxymethyl-2-naphthaleneacetic acid), is a non-steroidal, anti-inflammatory drug (NSAID) which exhibits analgesic and antipyretic properties. The exact mechanisms of action have not been clearly established but many of the effects of naproxen are associated with the inhibition of prostaglandin synthesis and in particular cyclo-oxygenase, an enzyme that catalyzes the formation of prostaglandin precursors from arachidonic acid. Naproxen is used to relieve mild to moderately severe pain in rheumatoid arthritis, osteoarthritis and other inflammatory complaints.

Naproxen has been available for use over a decade and has been found to be acceptably non-toxic by many regulatory agencies. Naproxen is used as either its free acid or its sodium salt, naproxen sodium. The present application concerns a naproxen sodium formulation, however, it will be understood that naproxen free acid could also be used.

Naproxen and naproxen sodium are conventionally administered on a two to four times daily basis. Plasma naproxen concentrations of 30–90 µg/ml reportedly are required for anti-inflammatory or analgesic effects. Reduced pain intensity has been demonstrated in sixty postpartum women from 0.5 to 6 hours after oral administration of naproxen or its sodium salt in doses sufficient to yield plasma naproxen levels between 30–70 µg/ml. Sevelius, H. et al., Br. J. Clin. Pharmacol. 10, pp. 259–263 (1980). Evidence from twenty-four patients with rheumatoid arthritis suggested that clinical response occurred at plasma naproxen levels above 50 µg/ml. Day, R. O. et al., Clin. Pharmacol. Ther. 31, pp. 733–740 (1982). Thus, while the rate of absorption may affect the onset of analgesic activity, continued plasma levels of the drug are likely to be important in maintaining analgesia.

It is an object of the present invention to provide a controlled absorption naproxen formulation suitable for once-daily administration, and particularly one which demonstrates an initial rate of absorption resulting in a rapid analgesic effect and then exhibits controlled absorption characteristics resulting in continued plasma levels of the drug over a 24 hour period.

SUMMARY OF THE INVENTION

Accordingly, the invention provides a naproxen formulation for oral administration on a once-daily basis, said formulation comprising a first portion of the naproxen formulated in a multi-particulate pellet form designed to release the drug at such a rate as to maintain therapeutically effective blood levels substantially over 24 hours when administered each day on a once-daily basis and optionally, a second portion of said naproxen formulated so as to release the drug promptly following administration so as to obtain a relatively immediate therapeutic response.

Preferably said first portion is in pellet form comprising a core of naproxen or a pharmaceutically acceptable salt thereof in association with an organic acid, the naproxen component and the organic acid being present in a ratio of from 20:1 to 1:1, and a multi-layer membrane surrounding said core and containing a major proportion of a pharmaceutically acceptable film-forming, water insoluble polymer and optionally a minor proportion of a pharmaceutically acceptable film-forming, water soluble polymer, the number of layers in said membrane and the ratio of said water soluble to water insoluble polymer being effective to permit release of said naproxen from said pellet at a rate allowing controlled absorption thereof at therapeutically effective blood levels over a twenty four hour period following each daily oral administration. Preferred formulations of the present invention are those wherein the dissolution rate of said pellet, when measured in vitro in a type 1 dissolution basket apparatus according to U.S. Pharmacopoeia XXII in phosphate buffer at pH 7.2 and at 75 r.p.m. substantially corresponds to the following dissolution pattern:

a) from 0 to 50% of the total naproxen is released after 1 hour of measurement in said apparatus;

b) from 20 to 70% of the total naproxen is released after a total of 2 hours of measurement in said apparatus; and c) not less than 50% of the total naproxen is released after 4 hours of measurement in said apparatus.

When the dissolution rate of said pellet is measured in vitro in a type 2 dissolution paddle apparatus according to U.S. Pharmacopoeia XXII in phosphate buffer at pH 7.4 and at 50 r.p.m. the dissolution rate substantially corresponds to the following dissolution pattern:

a) from 20 to 70% of the total naproxen is released after 1 hour of measurement in said apparatus;

b) not less than 50% of the total naproxen is released after a total of 2 hours of measurement in said apparatus; and c) not less than 75% of the total naproxen is released after 4 hours of measurement in said apparatus.

The invention also provides a controlled absorption naproxen formulation for oral administration, comprising pellets as hereinbefore defined, said formulation including a sufficient quantity of a rapid release form of naproxen to ensure prompt achievement of analgesically effective blood levels together with the prolonged effects described above. Such formulations comprising rapid and prolonged release components preferably have a dissolution rate which when measured in a type 1 dissolution basket apparatus according to U.S. Pharmacopoeia XXII in phosphate buffer at pH 7.2 and at 75 r.p.m. substantially corresponds to the following dissolution pattern:

a) from 15 to 50% of the total naproxen is released after 0.5 hours of measurement in said apparatus;

b) from 25 to 75% of the total naproxen is released after 1 hour of measurement in said apparatus;

c) not less than 65% of the total naproxen is released after 4 hours of measurement in said apparatus.

When the dissolution rate of said pellet is measured in vitro in a type 2 dissolution paddle apparatus according to U.S. Pharmacopoeia XXII in phosphate buffer at pH 7.4 and at 50 r.p.m. the dissolution rate substantially corresponds to the following dissolution pattern:

a) from 25 to 60% of the total naproxen is released after 0.5 hours of measurement in said apparatus;

b) from 35 to 75% of the total naproxen is released after 1 hour of measurement in said apparatus; and c) not less than 65% of the total naproxen is released after 4 hours of measurement in said apparatus.

The applicants have found in the case of the above formulations of the present invention, that therapeutically effective blood levels can be maintained substantially over 24 hours with peak plasma levels occurring between 2 to 16 hours, preferably between 4 to 10 hours. The present invention defines this desired time to peak plasma level as the Tmax of the formulation.

Advantageously, the formulation comprises a blend of pellets as hereinbefore defined together with up to 60% by weight of said rapid release form of naproxen, preferably 20–45%.

Most preferably, the rapid release form of naproxen comprises a rapid release granulate.

The naproxen used in the preferred dosage forms of the present invention is in the form of a pharmaceutically acceptable salt thereof, especially the sodium salt thereof.

The organic acid is preferably represented by one or more of the following acids: adipic acid, ascorbic acid, citric acid, fumaric acid, malic acid, succinic acid or tartaric acid. Especially preferred acids are fumaric acid and citric acid.

The core also optionally contains a lubricant which is represented by one or more of the following: sodium stearate, magnesium stearate, stearic acid or talc. The naproxen and lubricant are preferably present in a ratio of from 10:1 to 200:1.

Preferably, the core comprises naproxen or a pharmaceutically acceptable salt thereof and the associated organic acid embedded in a polymeric material. The polymeric material may be rapidly soluble in water or insoluble in water or freely permeable to naproxen and water.

The term water soluble polymer as used herein includes polymers which are freely permeable to water, while the term water insoluble polymer as used herein includes polymers which are slightly permeable to water.

The polymeric material preferably consists solely of a water insoluble polymer or a polymer which is slightly permeable to water and aqueous solutions of naproxen. Alternatively, the polymeric material may consist solely of a water soluble polymer or a polymer which is freely permeable to aqueous solutions of naproxen and water. The polymeric material of the core may include a combination of a water insoluble polymer with a water soluble polymer. The ratio of water soluble/freely permeable to water insoluble/slightly permeable polymer is determined by the particular combination of polymers selected.

The water soluble polymer is suitably polyvinyl alcohol, polyvinylpyrrolidone, methyl cellulose, hydroxypropyl cellulose, agar, carrageenan, xanthan, hydroxypropylmethyl cellulose or polyethylene glycol or a mixture thereof. An especially preferred water soluble polymer is polyvinylpyrrolidone.

A suitable polymer which is freely permeable to naproxen and water is a polymer sold under the Trade Mark EUDRAGIT RL.

The water insoluble polymer of the core is suitably ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly (ethylene), poly(ethylene) low density, poly(ethylene) high density, poly(propylene), poly(ethylene oxide), poly(ethylene terephthalate), poly (vinyl isobutyl ether), poly(vinyl acetate), poly(vinyl chloride) or polyurethane or a mixture thereof.

The water insoluble polymer of the core may also comprise naturally occurring polymers or resins. Especially suitable water insoluble, naturally occurring polymers include shellac, chitosan, gumjuniper or a mixture thereof.

A suitable polymer which is slightly permeable to naproxen and water is a polymer sold under the Trade Mark EUDRAGIT RS or a polymer whose permeability is pH dependent and sold under the Trade Mark EUDRAGIT L, EUDRAGIT S or EUDRAGIT E. Especially preferred polymers in this category are EUDRAGIT RS and EUDRAGIT L.

EUDRAGIT polymers are polymeric lacquer substances based on acrylates and/or methacrylates. The polymeric materials sold under the Trade Marks EUDRAGIT RL and EUDRAGIT RS are acrylic resins comprising copolymers of acrylic and methacrylic acid esters with a low content of quaternary ammonium groups and are described in the "EUDRAGIT" brochure of Messrs. Rohn Pharma GmbH (1985) wherein detailed physical-chemical data of these products is given. The ammonium groups are present as salts and give rise to the permeability of the lacquer films. EUDRAGIT RL and RS are freely permeable (RL) or slightly permeable (RS), respectively, independent of pH.

EUDRAGIT L is an anionic polymer synthesized from methacrylic acid and methacrylic acid methyl ester. It is insoluble in acids and pure water. It becomes soluble in a neutral to weakly alkaline milieu by forming salts with alkalis. The permeability of EUDRAGIT L is pH dependent. Above pH 5.0, the polymer becomes increasingly permeable. EUDRAGIT L is described in the "EUDRAGIT L" brochure of Messrs. Rohn Pharma GmbH (1986) wherein detailed physical-chemical data of the product is given.

The core suitably has a number of layers of the core-forming materials and is built up in a manner known per se.

A multi-layer arrangement of naproxen, organic acid and polymeric material is preferably built up on a central active core. The active core is formed by blending naproxen, organic acid and polymeric material to form a homogenous powder. A portion of the above blend is shaped to form a central core. A multi-layer arrangement is then built up by a successive layering and binding process where the remainder of the blend and a polymer binding solution are applied to the active core in alternate layers in a conventional coating pan. Alternatively, an automatic coating system may be used where the remainder of the blend and polymer binding solution is applied to the active core, simultaneously. Conventional automated coating systems include, for example, a CF granulator or a Glatt fluidized bed. The cores are formed to assure a uniform distribution of naproxen and excipient ingredients throughout the core. The preferred average diameter of the completed cores is in the range of 0.4 to 1.6 mm, an especially preferred average diameter being in the range of 0.6 to 1.1 mm.

The multi-layer arrangement of naproxen, organic acid and polymeric material may also be built up on a central inert core, suitably consisting of a non-pareil bead or seed of sugar/starch having an average diameter in the range 0.2–1.4 mm, especially 0.3–0.8 mm. The naproxen, organic acid and polymeric material may be built up on a central inert core as hereinbefore defined in a conventional coating pan or any automated coating system.

The naproxen, organic acid and optional other components are blended to form a homogenous powder. The naproxen component and organic acid component are preferably present in a ratio of from 20:1 to 1:2, more especially 6:1 to 1:1. The blend is suitably passed through an appropriate mesh screen using a milling machine. In the case of coating in a conventional coating pan, alternate layers of a coating solution/suspension of the polymeric material and the powder are applied to the central inert core to build up the multi-layer arrangement of the core. In the case of an automatic coating system, the coating solution/suspension of the polymeric material and the powder are applied, simultaneously, in conventional manner. The coating solution/suspension of the polymeric material comprises one or more polymers dissolved/suspended in a suitable solvent or mixture of solvents. The concentration of the polymeric material in the coating solution/suspension is determined by the viscosity of the final solution/suspension. Preferably, between 5 and 60 parts of the central inert cores are used relative to the homogenous powder. The addition of a plasticizing agent to the polymeric solution/suspension may be necessary depending on the formulation to improve the elasticity and also the stability of the polymer film and to prevent changes in the polymer permeability over prolonged storage. Such changes could affect the drug release rate. Suitable plasticizing agents include polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and varying percentages of acetylated monoglycerides.

As mentioned above, the core may optionally contain a lubricant. A preferred range of naproxen to lubricant ratio when a central inert core is used is 50:1 to 5:1.

Preferred coating materials include—solutions/suspensions of the polymers cited for use in the application of the powder blend to the central cores in a suitable organic/aqueous carrier medium.

The membrane of the film-forming polymer or mixture of polymers surrounding the core preferably has a proportion of a polymer which is slightly permeable to naproxen and water and optionally a proportion of a water permeable polymer, the ratio of slightly water permeable to water permeable polymer being determined by the inherent permeability characteristics of the polymer selected.

The membrane may also be composed of a proportion of a polymer which is water insoluble and a proportion of a polymer which is water soluble, the ratio of water insoluble to water soluble polymer being determined by the inherent permeability of the respective polymers.

Normally the ratio of water insoluble/slightly permeable polymers to water soluble/permeable polymers lies between 1:5 and 50:1, more usually 1:2 to 20:1. Examples of each of these types of polymer are described above. Especially useful water soluble/permeable polymers include polyvinylpyrrolidone, polyvinyl alcohol and EUDRAGIT RL while useful water insoluble/slightly permeable polymers include ethylcellulose, cellulose acetate, EUDRAGIT RS, EUDRAGIT L, EUDRAGIT E and EUDRAGIT S. Commercially available ready-made polymeric solutions/suspensions may also be useful. These ready-made solutions/suspensions may optionally contain plasticizing agents to improve the polymer film as described previously. Examples of ready-made solutions/suspensions of polymeric material with or without plasticizing agent include EUDRAGIT RL 30D, EUDRAGIT NE 30D, EUDRAGIT E 12.5, EUDRAGIT L 12.5 P, EUDRAGIT E 12.5, EUDRAGIT S 12.5 P, EUDRAGIT RL 12.5, EUDRAGIT RS 30D, EUDRAGIT RS 12.5, AQUACOAT (a Trade Mark of FMC Corporation) and SURE-LEASE (a Trade Mark of Colorcon Inc.).

The water insoluble polymer of the membrane may also comprise naturally occurring polymers or resins. Especially suitable water insoluble, naturally occurring polymers include shellac, chitosan, gumjuniper or a mixture thereof.

The membrane may be built up by applying a plurality of coats of membrane polymer solution or suspension to the core as hereinbefore described. The membrane solution or suspension contains the polymer(s) dissolved or suspended, respectively, in a suitable aqueous or organic solvent or mixture of solvents, optionally in the presence of a lubricant. Suitable lubricants are talc, stearic acid, magnesium stearate and sodium stearate. A particularly preferred lubricant is talc. The membrane, polymer or mixture of polymers may optionally include a plasticizing agent, the function and choice of which has been previously described.

The dissolution rate achieved is proportionally slower as the amount of membrane applied is increased.

The membrane solution or suspension may be applied to the active cores in a conventional coating pan as indicated or, alternatively, using an automated system such as a CF granulator, for example, a FREUND CF granulator, a GLATT fluidized bed processor, an AEROMATIC, a modified ACCELA-COTA or any other suitably automated bead coating equipment (FREUND, GLATT, AEROMATIC and ACCELA-COTA are all Trade Marks).

Preferably 2–75 ml of membrane solution/suspension is applied per application per kilogram of cores. In an automated system the total amount of membrane solution/suspension applied to the cores is the same as that applied in a conventional coating pan, except that the membrane solution/suspension may be applied continuously.

Preferably, when a coating pan is used the membrane is applied at a rate of 5–30 applications/day until all of the applications have been applied. Between days the pellets are dried for a suitable period of time at a controlled temperature.

The pellets and granulate may be compressed into tablets using a binder and/or hardening agent commonly employed in tableting such as microcrystalline cellulose sold under the Trade Mark "AVICEL" or a co-crystallized powder of highly modified dextrins (3% by weight) and sucrose sold under the Trade Mark "DI-PAC" in such a way that the specific dissolution rate of the pellets is maintained.

The pellets by themselves or combined with naproxen powder or naproxen cores may also be filled into hard or soft gelatine capsules.

Thus the Applicants have incorporated multi-particulate pellets of the sodium salt of naproxen into a tablet base. These multi-particulate pellets are formulated with sustained release characteristics allowing a continuous supply of naproxen to be maintained in the plasma to achieve a prolonged analgesic effect. On administration of the naproxen formulations of the present invention, the formulation, preferably a tablet, rapidly dissociates, releasing the pellets over a wide area of the GI tract. Thus, the number of gastrointestinal absorption sites is increased minimizing the occurrence of adverse GI effects often associated with the administration of NSAID's such as naproxen. The subject naproxen tablet formulation therefore is ideally suited to a once-daily dosage regimen having the potential for fewer associated adverse GI effects.

BRIEF DESCRIPTION OF THE DRAWING

The accompanying FIGURE is a graph of mean plasma levels (ug/ml) versus time (hours) for a naproxen formulation according to the invention relative to two reference naproxen formulations.

DETAILED DESCRIPTION OF THE INVENTION

Figure 1:
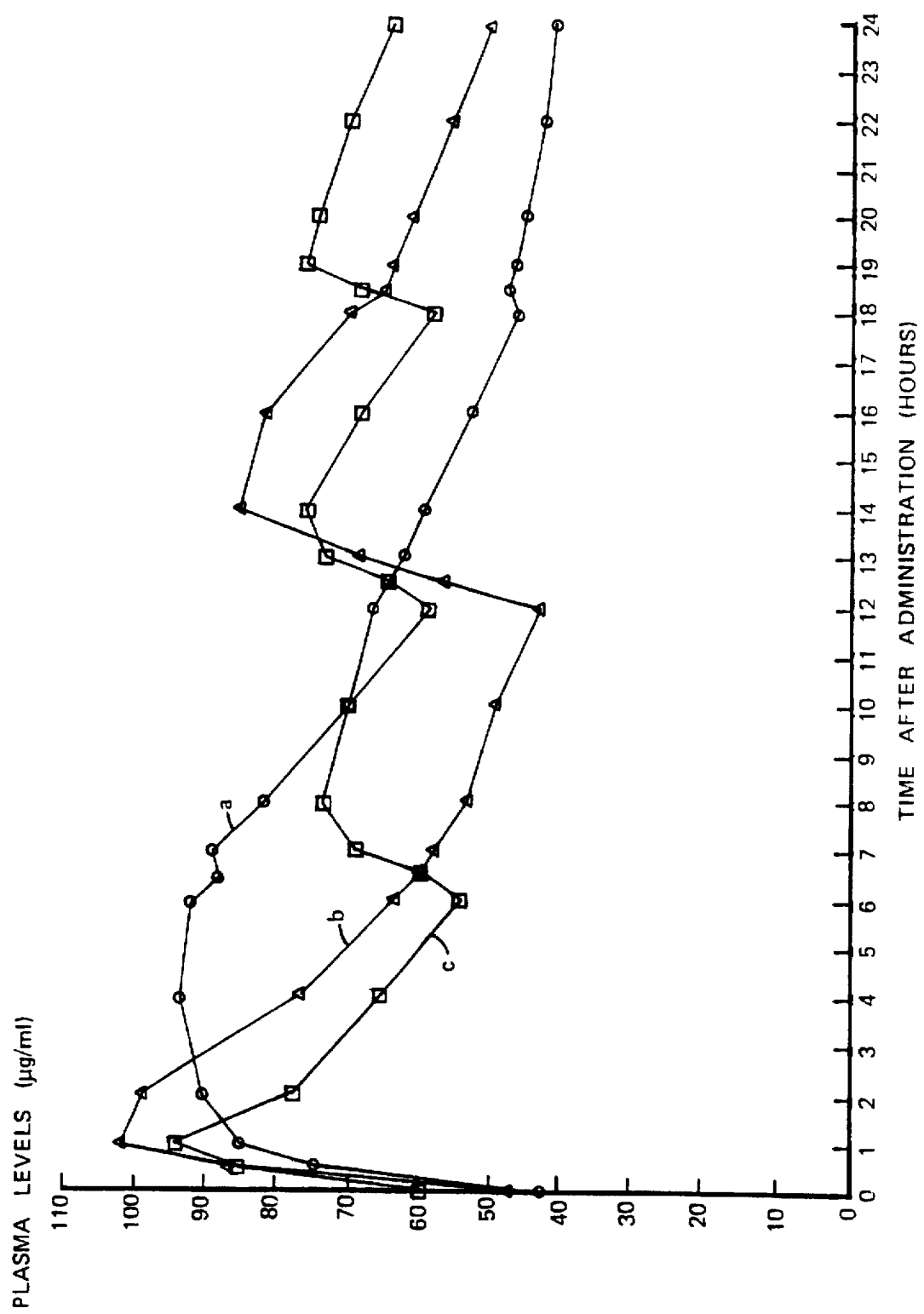

The invention will be further illustrated by the following Examples:

EXAMPLE 1

Naproxen sodium (50 kg), citric acid (14.286 kg), sodium lauryl sulphate (1.071 kg) and talc (3.571 kg) were blended and milled through a suitable mesh screen so as to obtain a homogenous powder.

The powder was applied to starch/sugar seeds (0.3–0.425 mm diameter) (4.286 kg) using a FREUND CF granulator and a coating solution of 3.5% polyvinylpyrrolidone in isopropanol to form the cores.

A membrane was then applied to the cores by spraying on a solution consisting of:

| | |
|---|---|
| 12.5% EUDRAGIT RS in acetone/isopropanol 40:60 | 50 parts by weight |
| 12.5% EUDRAGIT RL in acetone/isopropanol 40:60 | 40 parts by weight |
| 12.5% EUDRAGIT L in acetone/isopropanol 40:60 | 10 parts by weight |
| Isopropanol | 100 parts by weight | while at the same time but separately dusting on talc (100 parts by weight) in conventional manner. The ratio of membrane solution to talc applied was 0.62 grams of talc per gram of membrane solution. A sufficient amount of membrane solution and talc was applied to 76.214 kg of cores to achieve the dissolution profile given below.

The finished pellets were dried to evaporate all solvents prior to performing the dissolution profile.

A wet granulation of naproxen sodium (29.100 kg) and polyvinylpyrrolidone (K30) (0.900 kg) was prepared by adding isopropanol (8.2351 kg) slowly with mixing. Mixing was continued until a uniform mass was produced. The granulation was dried for a minimum of 12 hours at a temperature of not less than 45° C. The dried granulation was then passed through an oscillating granulator.

Naproxen sodium pellets (27.216 kg) and naproxen granulate (8.112 kg) were blended with additional tableting excipients:

| | |
|---|---|
| Microcrystalline cellulose | 15.372 kg |
| Crosspovidone | 1.040 kg |
| Magnesium stearate | 0.260 kg | and pressed into uncoated tablets.

Slight adjustments may be made in the above quantities to ensure a target tablet potency of 500 mg of naproxen.

The naproxen tablets were coated with an aqueous film coat. To do so, 0.350 kg of Opadry White OY-D-7192 was weighed and slowly added with mixing to 1.400 kg of purified water. Mixing was continued for 30 minutes. 10 kg of uncoated tablets were weighed and placed in an ACCELA-COTA. The coating was sprayed onto the tablets at a rate of 30–70 g per minute until coating was complete.

The dissolution rate of the pellets prepared above, prior to mixing with the granulate, was tested by the method of the U.S. Pharmacopoeia XXII Basket Method in phosphate buffer at pH 7.2 at 75 r.p.m. The naproxen sodium was quantitatively determined using u.v. spectrophotometry at 331 nm.

The dissolution rate was as follows:

| Time (h) | % Naproxen Sodium Released |
|---|---|
| 1 | 11.2 |
| 2 | 42.6 |
| 4 | 80.3 |

The dissolution rate of the coated tablets was tested and determined to be as follows:

| Time (h) | % Naproxen Sodium Released |
|---|---|
| 0.5 | 36.8 |
| 1 | 50.5 |
| 4 | 95.3 |

When tested by the method of the U.S. Pharmacopoeia XXII Paddle Method in phosphate buffer at pH7.4 and at 50 r.p.m., the dissolution rate for the pellets was as follows:

| Time (h) | % Naproxen Sodium Released |
|---|---|
| 1 | 24.6 |
| 2 | 64.2 |
| 4 | 77.3 |

The dissolution rate of the coated tablets was:

| Time (h) | % Naproxen Sodium Released |
|---|---|
| 0.5 | 44.1 |
| 1 | 73.5 |
| 4 | 96.0 |

Example 2

Naproxen sodium (15.41 kg), citric acid (4.40 kg) and talc (0.200 kg) were blended and milled through a suitable mesh screen to obtain a homogeneous powder. This powder blend was layered into spherical cores using a FREUND CF granulator or a GLATT and a coating solution of 12.5% EUDRAGIT RS in isopropanol.

A membrane was then applied to the cores by spraying on a solution consisting of:

| | |
|---|---|
| 12.5% EUDRAGIT RS in acetone/isopropanol | 70 parts by weight |
| 12.5% EUDRAGIT RL in acetone/isopropanol 40:60 | 10 parts by weight |
| 12.5% EUDRAGIT L in acetone/isopropanol 40:60 | 20 parts by weight |
| Isopropanol | 100 parts by weight | while at the same time but separately dusting on talc (40 parts by weight) in the conventional manner. The ratio of membrane solution to talc applied was 0.25 grams of talc per gram of membrane solution. A sufficient amount of membrane solution and talc was applied to 20.00 kg of cores to achieve the dissolution profile given below.

The finished pellets were dried to evaporate all solvents prior to performing the dissolution test.

A wet granulation of naproxen sodium (9.700 kg) and polyvinylpyrrolidone (K30) (0.300 kg) was prepared by adding isopropanol (2.745 kg) slowly with mixing. Mixing was continued until a uniform mass was produced. The granulation was dried for a minimum of 12 hours at a temperature of not less than 45° C. The dried granulation was then passed through an oscillating granulator.

Naproxen sodium pellets (24 kg) and naproxen granulate (7.9) kg) were blended with additional tableting excipients:

| | |
|---|---|
| Microcrystalline cellulose | 4.63 kg |
| Crosspovidone | 0.76 kg |
| Magnesium stearate | 0.19 kg |
| PVP K30 | 0.76 kg | and pressed into uncoated tablets.

Slight adjustments may be made in the above quantities to ensure a target tablet potency of 500 mg of naproxen.

The naproxen tablets were coated with an aqueous film coat. To do so, 0.350 kg of Opadry White OY-D-7192 was weighed and slowly added with mixing to 1.400 kg of purified water. Mixing was continued for 30 minutes. 10 kg of uncoated tablets were weighed and placed in an ACCELA-COTA. The coating was sprayed onto the tablets at a rate of 30-70 g per minute until coating was complete.

The dissolution rate of the pellets prepared above, prior to mixing with the granulate, was tested by the method of the U.S. Pharmacopoeia XXII Basket Method in phosphate buffer at pH 7.2 at 75 r.p.m. The naproxen sodium was quantitatively determined using u.v. spectrophotometry at 331 nm.

The dissolution rate was as follows:

| Time (h) | % Naproxen Sodium Released |
|---|---|
| 1 | 23.9 |
| 2 | 36.6 |
| 4 | 61.3 |

The dissolution rate of the coated tablets was tested and determined to be as follows:

| Time (h) | % Naproxen Sodium Released |
|---|---|
| 1 | 60.0 |
| 2 | 78.3 |
| 4 | 89.2 |

When tested by the method of the U.S. Pharmacopoeia XXII Paddle Method in phosphate buffer at pH 7.4 and at 50 r.p.m., the dissolution rate for the pellets was as follows:

| Time (h) | % Naproxen Sodium Released |
|---|---|
| 1 | 60.1 |
| 2 | 68.5 |
| 4 | 75.0 |

The dissolution rate of the coated tablets was:

| Time (h) | % Naproxen Sodium Released |
|---|---|
| 0.5 | 69.4 |
| 1 | 88.0 |
| 4 | 91.2 |

Example 3

Naproxen sodium (25 kg), citric acid (7.141 kg) and talc (0.325 kg) were blended and milled through a suitable mesh screen so as to obtain a homogenous powder. This powder blend was divided into two portions and layered into spherical cores using a FREUND CF granulator or a GLATT and a coating solution of 12.5% EUDRAGIT RS in isopropanol.

A membrane was then applied to the cores by spraying on a solution consisting of:

| | |
|---|---|
| 12.5% EUDRAGIT RS in acetone/isopropanol 40:60 | 75 parts by weight |
| 12.5% EUDRAGIT RL in acetone/isopropanol 40:60 | 25 parts by weight |
| Isopropanol | 100 parts by weight | while at the same time but separately dusting on talc (10 parts by weight) in the conventional manner. The ratio of membrane solution to talc applied was 0.06 grams of talc per gram of membrane solution. A sufficient amount of membrane solution and talc was applied to 32.4 kg of cores to achieve the dissolution profile given below.

The finished pellets were dried to evaporate all solvents prior to performing the dissolution test.

A wet granulation of naproxen sodium (19.400 kg) and polyvinylpyrrolidone (K30) (0.600 kg) was prepared by adding isopropanol (1.529 kg) slowly with mixing. Mixing was continued until a uniform mass was produced. The granulation was dried for a minimum of 12 hours at a temperature of not less than 45° C. The dried granulation was then passed through an oscillating granulator.

Naproxen sodium pellets (25 kg) and naproxen granulate (7.85 kg) were blended with additional tableting excipients:

| | |
|---|---|
| Microcrystalline cellulose | 6.00 kg |
| Crosspovidone | 0.815 kg |
| Magnesium stearate | 0.200 kg |
| PVP K30 | 0.815 kg | and pressed into uncoated tablets.

Slight adjustments may be made in the above quantities to ensure a target tablet potency of 500 mg of naproxen.

The naproxen tablets were coated with an aqueous film coat. To do so, 0.350 kg of Opadry White OY-D-9400 was weighed and slowly added with mixing to 1.400 kg of purified water. Mixing was continued for 30 minutes. 10 kg of uncoated tablets were weighed and placed in an ACCELA-COTA. The coating was sprayed onto the tablets at a rate of 30-70 g per minute until coating was complete.

The dissolution rate of the pellets prepared above, prior to mixing with the granulate, was tested by the method of the U.S. Pharmacopoeia XXII Basket Method in phosphate buffer at pH 7.2 at 75 r.p.m. The naproxen sodium was quantitatively determined using u.v. spectrophotometry at 331 nm.

The dissolution rate was as follows:

| Time (h) | % Naproxen Sodium Released |
| --- | --- |
| 1 | 30.1 |
| 2 | 42.5 |
| 4 | 67.5 |

The dissolution rate of the coated tablets was tested and determined to be as follows:

| Time (h) | % Naproxen Sodium Released |
| --- | --- |
| 0.5 | 39.6 |
| 1 | 55.0 |
| 4 | 90.0 |

EXAMPLE 4

Naproxen acid (50 kg), citric acid (15.64 kg), sodium lauryl sulphate (0.071 kg) and talc (0.500 kg) were blended and milled through a suitable mesh screen to obtain a homogeneous powder. This powder blend was layered into spherical cores using a FREUND CF granulator or a GLATT and a coating solution of 12.5% EUDRAGIT RS in isopropanol.

A membrane was then applied to the cores by spraying on a solution consisting of:

| | |
| --- | --- |
| 12.5% EUDRAGIT RS in acetone/isopropanol 40:60 | 90 parts by weight |
| 12.5% EUDRAGIT RL in acetone/isopropanol 40:60 | 10 parts by weight |
| Isopropanol | 100 parts by weight | while at the same time but separately dusting on talc (20 parts by weight) in the conventional manner. The ratio of membrane solution to talc applied was 0.125 grams of talc per gram of membrane solution. A sufficient amount of membrane solution and talc was applied to 66.22 kg of cores to achieve the dissolution profile given below.

The finished pellets were dried to evaporate all solvents prior to performing the dissolution test. The dissolution rate of the pellets was tested by the method of the U.S. Pharmacopoeia XXII Basket Method in phosphate buffer, at pH 7.2 at 75 r.p.m.

The naproxen was quantitatively determined using u.v. spectrophotometry at 331 nm.

The dissolution rate was as follows:

| Time (h) | % Naproxen Released |
| --- | --- |
| 1 | 23.9 |
| 2 | 36.6 |
| 4 | 61.3 |

EXAMPLE 5

Naproxen cores were prepared according to Example 1.

A membrane was then applied to the cores by spraying on a suspension of:

| | |
| --- | --- |
| 30% EUDRAGIT RS in water | 30 parts by weight |
| 30% EUDRAGIT RL in water | 6 parts by weight |
| talc | 6 parts by weight |
| water | 50 parts by weight |

The remaining 8 parts by weight were made up by a 9:1 mixture of tributylacetyl citrate, a plasticizer, and simethicone, an antifoam agent.

A sufficient amount of membrane solution was applied to achieve the following desired release rate.

| Time (h) | % Naproxen Sodium Released |
| --- | --- |
| 1 | 29.8 |
| 2 | 47.7 |
| 4 | 73.6 |

EXAMPLE 6

Naproxen cores were prepared according to Example 3.

A membrane was then applied to the cores by spraying on a suspension of:

| | |
| --- | --- |
| 30% EUDRAGIT RS in water | 40 parts by weight |
| 30% EUDRAGIT RL in water | 2 parts by weight |
| talc | 6 parts by weight |
| water | 50 parts by weight |

The remaining 2 parts by weight were made up by a 9:1 mixture of tributylacetyl citrate, a plasticizer, and simethicone, an antifoam agent.

A sufficient amount of membrane solution was applied to achieve the desired release rate of:

| Time (h) | % Naproxen Sodium Released |
| --- | --- |
| 1 | 14.5 |
| 2 | 42.7 |
| 4 | 71.1 |

EXAMPLE 7

Naproxen sodium (30.0 kg), citric acid (5.00 kg) and talc (0.400 kg) were blended and milled through a suitable mesh screen to obtain a homogeneous powder. This powder blend was layered into spherical cores using a FREUND CF granulator or a GLATT and a coating solution of 12.5% EUDRAGIT RS in isopropanol.

A membrane was then applied to the cores by spraying on a solution consisting of:

| | |
| --- | --- |
| 12.5% EUDRAGIT RS in acetone/isopropanol 40:60 | 85 parts by weight |
| 12/5% EUDRAGIT RL in acetone/isopropanol 40:60 | 15 parts by weight |
| Isopropanol | 100 parts by weight | while at the same time but separately dusting on talc (40 parts by weight) in the conventional manner. The ratio of membrane solution to talc applied was 0.25 grams of talc per gram of membrane solution. A sufficient amount of membrane solution and talc was applied to 35.4 kg of cores to achieve the dissolution profile given below.

The finished pellets were dried to evaporate all solvents prior to performing the dissolution test.

A wet granulation of naproxen sodium (14.550 kg) and polyvinylpyrrolidone (K30) (0.450 kg) was prepared by adding isopropanol (4.116 kg) slowly with mixing. Mixing was continued until a uniform mass was produced. The granulation was dried for a minimum of 12 hours at a temperature of not less than 45° C. The dried granulation was then passed through an oscillating granulator.

Naproxen sodium pellets (35.0 kg) and naproxen granulate (8.10 kg) were blended with additional tableting excipients:

| Microcrystalline cellulose | 8.346 kg |
|---|---|
| Crosspovidone | 1.077 kg |
| Magnesium stearate | 0.270 kg |
| PVP K30 | 1.077 kg | and pressed into uncoated tablets.

Slight adjustments may be made in the above quantities to ensure a target tablet potency of 750 mg of naproxen.

The naproxen tablets were coated with an aqueous film coat. To do so, 0.350 kg of Opadry White OY-9400 was weighed and slowly added with mixing to 1.400 kg of purified water. Mixing was continued for 30 minutes. 10 kg of uncoated tablets were weighed and placed in an ACCELA-COTA. The coating was sprayed onto the tablets at a rate of 30–70 g per minute until coating was complete.

The dissolution rate of the pellets prepared above, prior to mixing with the granulate, was tested by the method of the U.S. Pharmacopoeia XXII Basket Method in phosphate buffer at pH 7.2 at 75 r.p.m. The naproxen sodium was quantitatively determined using u.v. spectrophotometry at 331 nm.

The dissolution rate was as follows:

| Time (h) | % Naproxen Sodium Released |
|---|---|
| 1 | 50.7 |
| 2 | 71.3 |
| 4 | 88.0 |

The dissolution rate of the coated tablets was tested and determined to be as follows:

| Time (h) | % Naproxen Sodium Released |
|---|---|
| 0.5 | 49.5 |
| 1 | 71.8 |
| 4 | 89.4 |

EXAMPLE 8

Naproxen Sodium (22.5 kg), citric acid (1.125 kg) and talc (0.251 kg) were blended and milled through a suitable mesh screen to obtain a homogeneous powder. This powder blend was layered into spherical cores using a FREUND CF granulator or a GLATT and a coating solution of 12.5% EUDRAGIT RS in isopropanol.

A membrane was then applied to the cores by spraying on a solution consisting of:

| 12.5% EUDRAGIT RS in acetone/isopropanol 40:60 | 70 parts by weight |
|---|---|
| 12.5% EUDRAGIT RL in acetone/isopropanol 40:60 | 10 parts by weight |
| 12.5% EUDRAGIT L in acetone/isopropanol 40:60 | 20 parts by weight |
| Isopropanol | 100 parts by weight | while at the same time but separately dusting on talc (5 parts by weight) in the conventional manner. The ratio of membrane solution to talc applid was 0.03 grams of talc per gram of membrane solution. A sufficient amount of membrane solution and talc was applied to 12.48 kg of cores to achieve the dissolution profile given below.

The finished pellets were dried to evaporate all solvents prior to performing the dissolution test.

A wet granulation of naproxen sodium (14.55 kg) and polyvinylpyrrolidonne (K30) (0.45 kg) was prepared by adding isopropanol (1.147 kg) slowly with mixing. Mixing was continued until a uniform mass was produced. The granulation was dried for a minimum of 12 hours at a temperature of not less than 45° C. The dried granulation was then passed through an oscillating granulator.

Naproxen sodium pellets (12.0 kg) and naproxen granulate (3.986 kg) were blended with additional tableting excipients:

| Microcrystalline cellulose | 2.32 kg |
|---|---|
| Crosspovidone | 0.58 kg |
| Magnesium stearate | 0.10 kg |
| PVP K30 | 0.39 kg | and pressed into uncoated tablets.

Slight adjustments may be made in the above quantities to ensure a target tablet potency of 750 mg of naproxen.

The naproxen tablets were coated with an aqueous film coat. To do so, 0.350 kg of Opadry White OY-D-7192 was weighed and slowly added with mixing to 1.400 kg of purified water. Mixing was continued for 30 minutes. 10 kg of uncoated tablets were weighed and placed in an ACCELA-COTA. The coating was sprayed onto the tablets at a rate of 30–70 g per minute until coating was complete.

The dissolution rate of the pellets prepared above, prior to mixing with the granulate, was tested by the method of the U.S. Pharmacopoeia XXII Basket Method in phosphate buffer at pH 7.2 at 75 r.p.m. The naproxen sodium was quantitatively determined using u.v. spectrophotometry at 331 nm.

The dissolution rate was as follows:

| Time (h) | % Naproxen Sodium Released |
|---|---|
| 1 | 23.9 |
| 2 | 36.6 |
| 4 | 61.4 |

The dissolution rate of the coated tablets was tested and determined to be as follows:

| Time (h) | % Naproxen Sodium Released |
|---|---|
| 0.5 | 40.8 |
| 1 | 70.0 |
| 4 | 87.0 |

Pharmacological Data for Naproxen Formulations

In Vivo Performance:

Pharmacological Data for Naproxen Formulation of Example 1

The naproxen formulation prepared in Example 1 was evaluated in vivo under steady state conditions.

A steady state study was performed in 18 healthy male volunteers, comparing the formulation of Example 1 with selected reference products, i.e., conventional immediate release tablets. The formulation of Example 1 was administered as a single tableted dose of 1,000 mg of naproxen at 0 hours on days 1-7, while reference Naprosyn (N), a commercially available naproxen formulation manufactured by Syntex which is administered twice daily, was administered as a single 500 mg tablet at 0 and 12 hours (i.e. b.i.d.) on days 1-7 and reference Synflex (S), a commercially available naproxen sodium formulation manufactured by Syntex which is administered three to four times daily, was administered as a single 250 mg dose at 0, 6, 12 and 18 hours (i.e. q.i.d.) on days 1-7. Plasma was sampled out to 24 hours and the mean results were calculated and tabulated. The results are illustrated in the accompanying Figure.

In the Figure, curve a) corresponds to a naproxen formulation prepared according to Example 1; curve b) corresponds to Reference (N); and curve c) corresponds to reference (S).

The data presented in Table 1 are from day 7 sampling.

TABLE 1

Mean Naproxen Concentrations (ug/ml) - Day 7

| Hour | Reference (N) | Reference (S) | Formulation of Example 1 |
|---|---|---|---|
| 0.0 | 46.95 | 59.80 | 42.39 |
| 0.50 | 86.41 | 84.92 | 74.95 |
| 1.00 | 102.09 | 94.33 | 84.89 |
| 2.00 | 99.33 | 77.63 | 90.15 |
| 4.00 | 76.38 | 65.05 | 93.09 |
| 6.00 | 63.34 | 53.90 | 91.22 |
| 6.50 | 59.20 | 58.21 | 87.26 |
| 7.00 | 57.10 | 68.53 | 88.48 |
| 8.00 | 52.76 | 72.98 | 80.64 |
| 10.00 | 48.56 | 69.52 | 69.02 |
| 12.00 | 41.16 | 57.07 | 65.68 |
| 12.50 | 55.27 | 62.46 | 63.52 |
| 13.00 | 67.12 | 72.45 | 60.83 |
| 14.00 | 83.94 | 74.81 | 57.78 |
| 16.00 | 80.05 | 67.10 | 51.26 |
| 18.00 | 68.39 | 55.96 | 44.37 |
| 18.50 | 63.09 | 66.89 | 45.84 |
| 19.00 | 62.14 | 74.40 | 44.63 |
| 20.00 | 58.99 | 72.92 | 42.89 |
| 22.00 | 53.39 | 68.11 | 39.97 |
| 24.00 | 47.90 | 61.38 | 38.30 |

The results of this in vivo comparison of the formulation of Example 1 against conventional immediate release tablets (References N and S) indicate the formulation of Example 1 to be bioequivalent (99.28%) to Reference N and bioequivalent (95.46%) to Reference S. Both Example 1 and Reference S formulations use the sodium salt of naproxen, the Reference N formulation, however, uses the free acid form of naproxen. Generally, peak plasma concentrations following administration of naproxen as its sodium salt are higher and are attained more rapidly than those following administration of naproxen as the free acid, hence the use of the sodium salt in the conventional form as an analgesic on a more frequent dosing regimen (3-4 times daily).

The Tmax value of the formulation of the present invention of 5.0 hours was significantly longer than that of Reference N at 1.36 hours, thus demonstrating the improved suitability of the present formulations in terms of maintaining naproxen plasma levels important for continued analgesia and anti-inflammatory effects up to 24 hours following administration. Furthermore, the formulation of Example 1 exhibited an extended mean plasma profile with adequate duration of time cover in the range of desired therapeutic plasma naproxen concentrations of 30-60 mcg/ml. Also, the mean Cmax value of the product of Example 1 was close to the Cmax values of the References, indicating that the sustained release characteristics of Example 1 did not adversely affect the maximum plasma levels attained following administration of the formulation.

A gastric tolerability questionnaire was completed by each subject on each day of the study. The results indicated a 47% reduction in adverse gastrointestinal effects for the formulation prepared according to Example 1 when compared to those recorded by Reference N or S.

The clinical efficacy of the naproxen formulation according to the present invention was evaluated in osteoarthritic patients. In osteoarthritis, NSAID's are primarily used for their analgesic rather than their anti-inflammatory effect, although inflammation may be part of the symptomatology. To evaluate the formulation of the present invention, the formulation of Example 1 was compared with Naprosyn in a double-blind double placebo controlled study in osteoarthritic patients.

Efficacy of both naproxen formulations was indicated by the degree of pain assessed by the patient on a visual analogue scale and was graded on a four point verbal rating scale. In addition, blood samples were analyzed for naproxen plasma concentrations and any adverse effects were recorded. A gastrointestinal tolerability questionnaire was completed by each volunteer at the end of each treatment period.

In summary, in terms of clinical efficacy, the naproxen formulation according to the present invention performed as well as the reference and was superior to the reference in terms of fewer gastrointestinal complaints and adverse events, thus demonstrating the safety and advantages of the multiparticulate formulations of the present invention when compared with the commercially available reference products.

We claim:

1. A naproxen formulation for once-daily oral administration comprising naproxen in a multi-particulate pellet form, each pellet having a core of naproxen or a pharmaceutically acceptable salt thereof in association with an organic acid, the naproxen or pharmaceutically acceptable salt thereof and the organic acid being present in a ratio of from 20:1 to 1:1, and a multi-layer membrane surrounding said core and containing a pharmaceutically acceptable film-forming, water insoluble polymer and optionally a pharmaceutically acceptable film-forming, water soluble polymer and having a dissolution rate which when measured in vitro in a type 1 dissolution basket apparatus according to U.S. Pharmacopoeia XXI in phosphate buffer at pH 7.2 and at 75 r.p.m. corresponds to the following dissolution pattern:

a) from 0 to 50% of the total naproxen is released after 1 hour of measurement in said apparatus;

b) from 20 to 70% of the total naproxen is released after 2 hours of measurement in said apparatus; and c) not less than 50% of the total naproxen is released after a total of 4 hours of measurement in said apparatus.

2. A pellet formulation according to claim 1, wherein the pellet has a dissolution rate which when measured in vitro in a type 2 dissolution paddle apparatus according to U.S. Pharmacopoeia XXII in phosphate buffer at pH 7.4 and at 50 r.p.m. corresponds to the following dissolution pattern:

a) from 20 to 70% of the total naproxen is released after 1 hour of measurement in said apparatus;

b) not less than 50% of the total naproxen is released after 2 hours of measurement in said apparatus; and c) not less than 75% of the total naproxen is released after a total of 4 hours of measurement in said apparatus.

3. A pellet formulation according to claim 1, wherein the organic acid is selected from the group consisting of adipic acid, ascorbic acid, citric acid, fumaric acid, maleic acid, succinic acid and tartaric acid.

4. A pellet formulation according to claim 1, wherein the naproxen or pharmaceutically acceptable salt thereof and organic acid are present in a ratio of 6:1 to 1:1.

5. A pellet formulation according to claim 1, wherein the core comprises naproxen or a pharmaceutically acceptable salt thereof and the associated organic acid embedded in one or more polymers.

6. A pellet formulation according to claim 5, wherein the one or more polymers are insoluble in water.

7. A pellet formulation according to claim 5, wherein the core comprises:

a) a powder mixture containing naproxen or a pharmaceutically acceptable salt thereof, an organic acid selected from adipic acid, ascorbic acid, citric acid, fumaric acid, malic acid, succinic acid and tartaric acid; and b) one or more polymers containing a proportion of a pharmaceutically acceptable water soluble or freely water permeable polymer and a proportion of a pharmaceutically acceptable water insoluble polymer, said core comprising layers of said powder mixture and said one or more polymers superimposed one upon the other and said one or more polymers forming an outer coat of said core.

8. A pellet formulation according to claim 5, wherein the naproxen, organic acid and one or more polymers are built up on a central active core.

9. A pellet formulation according to claim 8, wherein the active core is formed by blending the naproxen, organic acid and one or more polymers to form a homogenous powder, shaping a portion of said blend to form a central core and applying the remainder of said blend alternately or simultaneously with a polymer binding solution to form a layered structure on said central core.

10. A pellet formulation according to claim 5, wherein the naproxen, organic acid and one or more polymers are built up on an inert core.

11. A formulation according to claim 1, which contains naproxen sodium as the active ingredient.

12. A controlled absorption naproxen formulation for oral administration, comprising pellets according to claim 1, said formulation including a rapid release form of naproxen.

13. A controlled absorption naproxen formulation according to claim 12, having a dissolution rate which when measured in a type 1 dissolution basket apparatus according to U.S. Pharmacopoeia XXII in phosphate buffer at pH 7.2 and at 75 r.p.m. corresponds to the following dissolution pattern:

a) from 15 to 50% of the total naproxen is released after 0.5 hours of measurement in said apparatus;

b) from 25 to 75% of the total naproxen is released after 1 hour of measurement in said apparatus; and c) not less than 65% of the total naproxen is released after 4 hours of measurement in said apparatus.

14. A controlled absorption naproxen formulation according to claim 12, having a dissolution rate which when measured in a type 2 dissolution paddle apparatus according to U.S. Pharmacopoeia XXII in phosphate buffer at pH 7.4 and at 50 r.p.m. corresponds to the following dissolution pattern:

a) from 25 to 60% of the total naproxen is released after 0.5 hours of measurement in said apparatus;

b) from 35 to 75% of the total naproxen is released after 1 hour of measurement in said apparatus;

c) not less than 65% of the total naproxen is released after 4 hours of measurement in said apparatus.

15. A controlled absorption naproxen formulation according to claim 12, which comprises a blend of pellets, together with up to 60% by weight of a rapid release form of naproxen.

16. A capsule or tablet comprising a formulation according to claim 1.

17. A capsule or tablet comprising a formulation according to claim 12.

* * * * *